US009649120B1

(12) United States Patent
Gitlin et al.

(10) Patent No.: US 9,649,120 B1
(45) Date of Patent: May 16, 2017

(54) MINIMALLY INVASIVE SURGERY PLATFORM ATTACHMENT APPARATUS

(71) Applicants: University of South Florida, Tampa, FL (US); Innovatia Medical Systems L.L.C., St. Petersburg, FL (US)

(72) Inventors: Richard D. Gitlin, Tampa, FL (US); Adam Anderson, Tampa, FL (US); Shekhar Bhansali, Tampa, FL (US); Alexander Rosemurgy, Tampa, FL (US); Craig Lusk, Lutz, FL (US); Sharona Ross, Tampa, FL (US); Peter P. Savage, St. Petersburg, FL (US)

(73) Assignees: University of South Florida, Tampa, FL (US); Innovatia Medical Systems, L.L.C., St. Petersburg, FL (US)

( * ) Notice: Subject to any disclaimer, the term of this patent is extended or adjusted under 35 U.S.C. 154(b) by 299 days.

(21) Appl. No.: 14/500,259

(22) Filed: Sep. 29, 2014

Related U.S. Application Data

(63) Continuation-in-part of application No. 12/858,854, filed on Aug. 18, 2010, now abandoned.

(60) Provisional application No. 61/234,786, filed on Aug. 18, 2009.

(51) Int. Cl.
*A61B 17/29* (2006.01)

(52) U.S. Cl.
CPC .......... *A61B 17/29* (2013.01); *A61B 17/2909* (2013.01); *A61B 2017/2925* (2013.01); *A61B 2017/2945* (2013.01)

(58) Field of Classification Search
CPC ............ A61B 17/29; A61B 2017/2901; A61B 2017/2902; A61B 2017/2903; A61B 2017/2909; A61B 2017/2912; A61B 2017/2913; A61B 2017/2919; A61B 2017/292; A61B 2017/2926; A61B 2017/2927; A61B 2017/2946
See application file for complete search history.

(56) References Cited

U.S. PATENT DOCUMENTS 5,604,531 A   2/1997   Iddan et al.
6,315,721 B2  11/2001  Schulman et al.
6,322,578 B1  11/2001  Houle et al.
(Continued)

OTHER PUBLICATIONS

Hu et al., In-Vivo Pan/Tilt Endoscope with Integrated Light Source, IEEE/RSJ International Conference on Intelligent Robots and Systems, 2007, San Diego.
(Continued)

*Primary Examiner* — Todd J Scherbel
(74) *Attorney, Agent, or Firm* — Nilay J. Choksi; Smith & Hopen, P.A.

(57) ABSTRACT

An apparatus for the insertion, placement, attachment, and removal of a surgical device includes a handle and an elongate shaft. Opposing spring fingers that open and close relative to one another are partially and slidably disposed within the distal end of the elongate shaft opposite the handle. The opposing spring fingers are adapted to grasp a surgical device and power the surgical device via physical conductors on the spring fingers or graspers attached thereto, resulting in the surgical device being fully functional. A first trigger mechanism opens and closes the spring fingers via a piston disposed within the elongate shaft. A second trigger mechanism rotates the surgical device grasped by the spring fingers.

12 Claims, 8 Drawing Sheets

(56) References Cited

U.S. PATENT DOCUMENTS

| | | | |
|---|---|---|---|
| 6,402,689 B1 | 6/2002 | Scarantino et al. | |
| 6,546,272 B1 | 4/2003 | MacKinnon et al. | |
| 7,009,634 B2 | 3/2006 | Iddan et al. | |
| 7,214,182 B2 | 5/2007 | Shimizu et al. | |
| 8,416,342 B1 | 4/2013 | Gitlin et al. | |
| 2002/0143355 A1 | 10/2002 | Messerly | |
| 2005/0267555 A1 | 12/2005 | Marnfeldt et al. | |
| 2007/0255098 A1 | 11/2007 | Wang et al. | |
| 2007/0270651 A1 | 11/2007 | Gilad et al. | |
| 2010/0234866 A1* | 9/2010 | Arcenio | A61B 17/1671 606/170 |
| 2013/0060250 A1* | 3/2013 | Twomey | A61B 18/1447 606/52 |

OTHER PUBLICATIONS

Hu et al., Insertable Surgical Imaging Device with Pan, Tilt, Zoom, and Lighting, IEEE International Conference on Robotics and Automation, May 2008.

Hu et al., Insertable Stereoscopic 3D Surgical Imaging Device with Pan and Tilt, IEEE International Conference on Biomedical Robotics and Biomechatronics (BioRob 2008).

\* cited by examiner

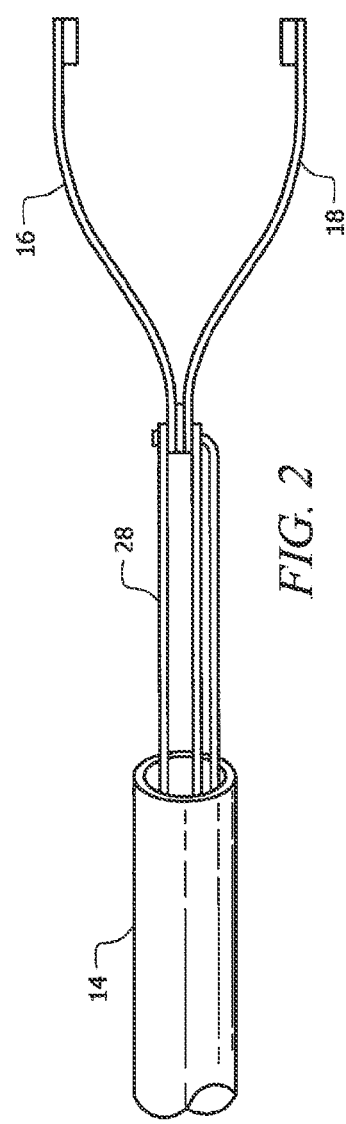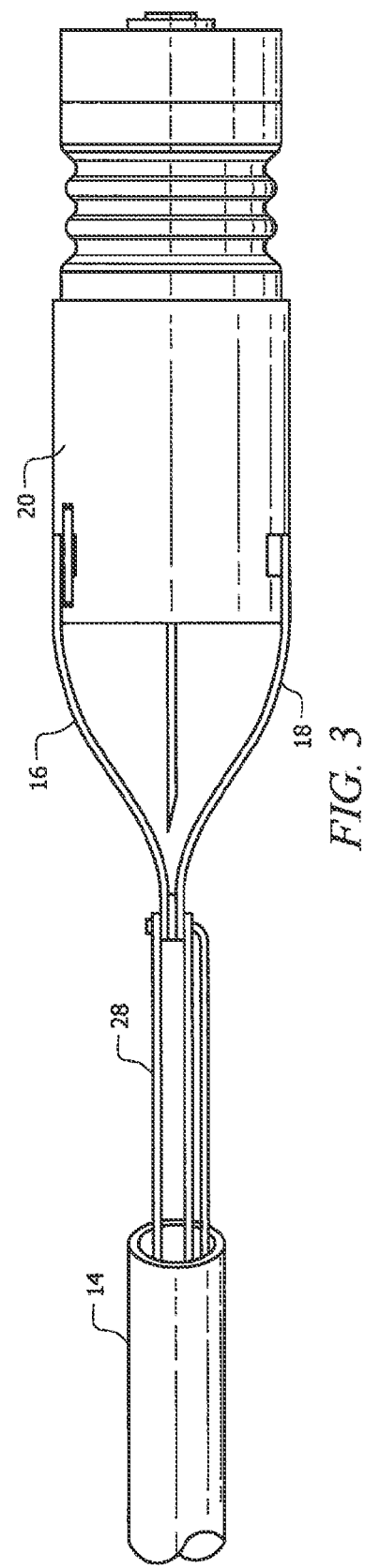

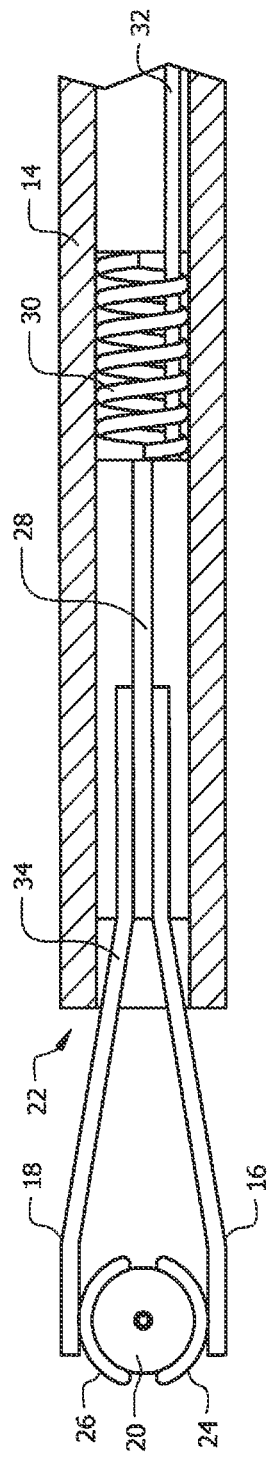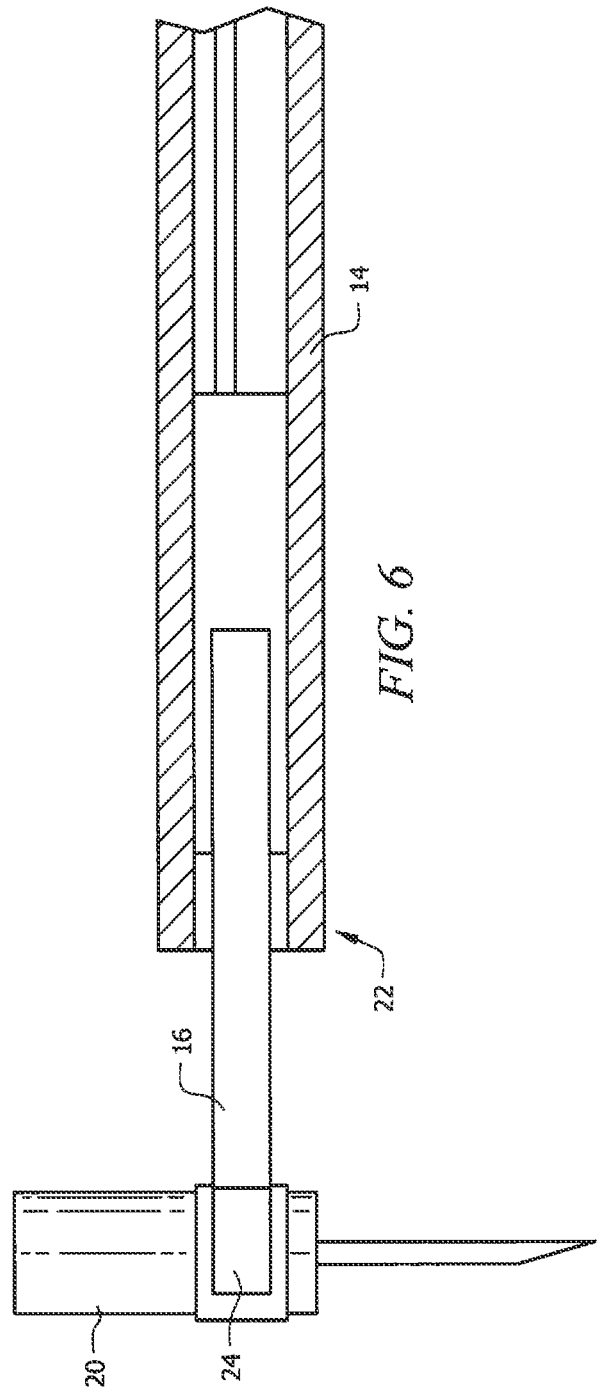
FIG. 5
FIG. 6

MINIMALLY INVASIVE SURGERY PLATFORM ATTACHMENT APPARATUS

CROSS REFERENCE TO RELATED APPLICATION

This application is a continuation of and claims priority to U.S. Nonprovisional patent application Ser. No. 12/858,854, entitled "Minimally Invasive Surgery Platform Attachment Apparatus", filed Aug. 18, 2010, which claims priority to U.S. Provisional Patent Application No. 61/234,786, entitled "Minimally Invasive Surgery Platform Attachment Apparatus", filed on Aug. 18, 2009, both of which are incorporated herein by reference in their entireties.

BACKGROUND OF THE INVENTION

1. Field of the Invention

This invention relates to minimally invasive surgery. More specifically, it relates to an attachment apparatus for the placement, attachment, and removal of a surgical device.

2. Description of the Prior Art

Minimally Invasive Surgery (MIS) is done through small incisions. For patients, MIS means less trauma to the body, less blood loss, smaller surgical scars, less need for pain medication, and shorter hospital stays. In recently developed MIS techniques (e.g., Natural Orifice Transluminal Endoscopic Surgery (NOTES) and Laparo-Endoscopic Single Site (LESS) surgery), "scarless" abdominal operations are performed with multiple endoscopic tools passing through a multiport trocar inserted in a natural body orifice (such as the umbilicus). Each year thousands of patients enjoy the benefits of these types of non-open surgeries.

While there are many benefits, these surgeries often take longer to perform than equivalent open surgeries, which results in additional patient risk to contamination. Additionally, LESS surgery creates a bottleneck for surgical tools through the four ports of the trocar where graspers, cutters, videoscopes, and insufflation tubes all compete for the limited number of trocar ports.

In order to eliminate this bottleneck, a family of insertable surgical modules has been proposed. The first member of the family is an autonomous videoscope that transmits video and is controlled wirelessly from outside the operational space inside the body. This device is the subject of U.S. Pat. No. 8,416,342 to Gitlin et al. and U.S. patent application Ser. No. 13/858,260 to Gitlin et al. In order to achieve the benefits of the proposed family of insertable surgical modules and to place other surgical tools inside the body, an insertion/removal tool is needed to decrease the surgical-tool bottleneck experienced by surgeons in single-site procedures. However, in view of the prior art considered as a whole at the time the present invention was made, it was not obvious to those of ordinary skill in the art how the limitations of the art could be overcome.

Certain attachment tools do exist in the prior art. For example. U.S. Patent Application Publication No. 2005/0267555 to Marnfeldt generally discusses a cannula that is positioned through a patient's skin for access into the interior of the patient to adjust positioning of an already-implanted medical device (as opposed to an insertable and withdrawable device, which tends to be temporary rather than more permanent and has different requirements from the Food and Drug Association). A variety of engagement tools and then be inserted through the cannula to retrieve the implanted medical device, and the engagement tool would then be manually retracted back through the cannula and out of the patient's body. In essence, Marnfeldt discusses a system having two major components (the cannula and the engagement tool) that are not connected to each other in any way.

Marnfeldt further includes a power source for the implanted medical device. In particular, Marnfeldt discusses an implantable stimulator which is a standalone device that is implanted into the patient's body. This implanted stimulator itself includes a power source, programmable memory, electrical circuitry, coil, and a pump. The power source in this implanted stimulator powers the remainder of the device. The implanted stimulator is wirelessly connected to external devices that can send information or power to the implanted stimulator. The power source in Marnfeldt is implanted into the body to power the components within that stimulator. A disadvantage of this methodology is the potential of the RF (i.e., electromagnetic) field to interfere with other devices.

For the internal power source to be recharged by an external source via an RF (electromagnetic) field, the coil of Marnfeldt must be an integral part of the implanted device. As such, there is no electrical or RF field connection between the graspers and the implantable device at any time in Marnfeldt. Further, the graspers taught in Marnfeldt show no ability to conduct electricity or to create an electromagnetic field, and in some configurations are single pieces that are incapable of supplying power, which requires at least two conductors or creation of an electromagnetic field. In other words, the graspers of Marnfeldt have no direct electrical connection with the implantable medical device. Rather, Marnfeldt "transfers power" to the battery of the implantable device via an electromagnetic field that creates an electrical transformer with an air, skin and tissue core, where the primary winding is located in the external source and the secondary winding is the coil which must be located in the implantable device. The use of a transformer requires AC current in the primary coil and results in AC current in the secondary coil. That AC current in the secondary winding/coil requires conversion to DC current via AC-to-DC conversion/rectifier circuitry within the implantable device to power the implantable device. U.S. Pat. No. 6,315,721 to Schulman et al. discusses charging or recharging an implanted/implantable medical device using an AC magnetic device. However, no direct electrical connection is formed, and use of electromagnetic field can potentially interfere with other devices, as previously noted.

As another example, U.S. Patent Application Publication No. 2002/0143355 to Messerly discusses an ultrasonic surgical instrument in a shears-type configuration for cutting targeted tissue. Messerly includes end-effectors that vibrate at ultrasonic frequencies and thus transmit ultrasonic energy to tissues to cut, dissect, or cauterize the tissue. By contrast, the arms and graspers of Applicant's claimed invention are utilized (via the first mechanism) to grab a medical device without cutting, dissecting, or cauterizing the medical device or any associated tissue. A disadvantage of this system, as opposed to the current invention which will become clearer as this specification continues, is that the ultrasonic energy does not power an implantable medical device and the end effectors cannot and must not be powered during insertion and removal of a surgical device. Otherwise, the end effector would be vibrating at ultrasonic frequencies, thus creating an active scalpel.

Accordingly, what is needed is a surgical tool that is capable of accurately positioning and directly powering implantable medical devices. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF INVENTION

The long-standing but heretofore unfulfilled need for an insertion/removal tool that accurately positions and directly powers implantable medical devices is now met by a new, useful, and nonobvious invention.

The novel attachment apparatus assists in the placement of a surgical device. It enables surgeons to undertake MIS safer, faster, and less invasively. The attachment apparatus is unique in that it alleviates surgical-tool bottleneck experienced by surgeons in single-site procedures and allows for the insertion, placement, attachment, and removal of an attached surgical device. Further, the attachment apparatus allows the insertion, placement, attachment, de-attachment and removal of insertable/implantable medical devices while the devices are powered (by the apparatus) and fully functional during the procedure.

More particularly, the novel attachment apparatus includes a handle and an elongate shaft. Opposing spring fingers that open and close relative to one another are partially and slidably disposed within the distal end of the elongate shaft opposite the handle. The opposing spring fingers are adapted to grasp a surgical device. For example, the opposing spring fingers can include a pair of diametrically opposed partial cylinder graspers for grasping the medical device. The opposing spring fingers and/or diametrically opposed partial cylinder graspers are electrically conducive for supply power to the implantable medical device.

A first trigger mechanism is cooperatively positioned within the handle and is in mechanical communication with the opposing spring fingers via a piston. The piston advances and retracts the opposing spring fingers when the first trigger mechanism is engaged. In an embodiment, the piston includes a compression spring, actuating rod, and a hard stop along the inner diameter of the distal end of the elongate shaft.

A second trigger mechanism is also cooperatively positioned within the handle and is in mechanical communication with the opposing spring fingers. The second trigger mechanism rotates the surgical device grasped by the opposing spring fingers from a first insertion position (which aligns the surgical device with the axis of the elongate shaft) to a second placement position when the second trigger mechanism is engaged. The placement position is variable through a range of motion to accommodate the attachment process.

Accordingly, it is an object of the present invention to assist a surgeon in the insertion, placement, attachment, and removal of a surgical device. It is a further object of the present invention to power the surgical device during this procedure via direct contact with the apparatus during insertion, placement, attachment, and removal of the surgical device.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 2 is a top view of a grasping portion of an attachment apparatus.

FIG. 3 is a top view of a grasping portion of an attachment apparatus grasping a surgical device.

FIG. 5 is a top view of a grasping portion of an attachment apparatus grasping a surgical device in a rotated position.

FIG. 6 is a side view of a grasping portion of an attachment apparatus grasping a surgical device in a rotated position.

DETAILED DESCRIPTION OF THE PREFERRED EMBODIMENT

Figure 1:
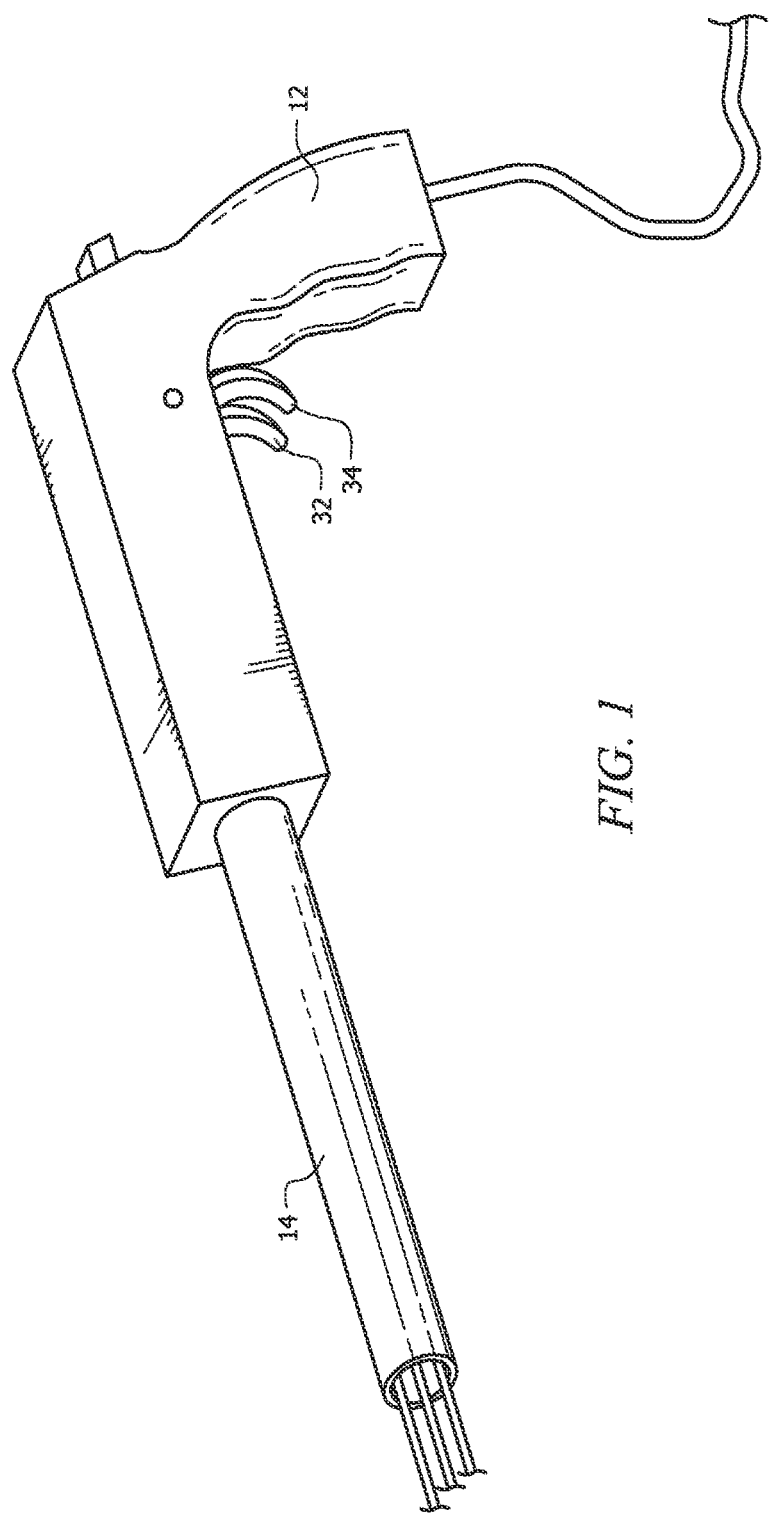
FIG. 1 is a perspective view of a handle portion of an attachment apparatus.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

The invention provides an apparatus for the insertion, placement, attachment, and removal of a surgical device. The attachment apparatus is unique in that it alleviates surgical-tool bottleneck experienced by surgeons in single-site procedures and allows for the insertion, placement, attachment, and removal of an attached surgical device. Although the apparatus may be used in conjunction with any surgical device, the following detailed description discusses the attachment apparatus being used in conjunction with a cable-free capsule camera module (CM), to be known commercially as a MARVEL platform. The camera module is attached to the inner abdominal wall of a patient. The attachment apparatus assists in the insertion and placement of the camera module.

In an embodiment, the current invention further is an instrument that provides power to the insertable/implantable medical device while the medical device is being inserted into, attached to, detached from, and removed from the subject via direct contact with the instrument, such that the medical device is fully operational throughout the process or procedure.

As collectively depicted in FIGS. 1-11, the novel attachment apparatus includes handle 12 having elongate shaft 14 extending there from. Opposing spring fingers 16 and 18 open and close relative to one another and are partially and slidably disposed within the distal end 22 of elongate shaft 14 opposite handle 12. Opposing spring fingers 16 and 18 are adapted to grasp and supply power to a surgical device 20, e.g., the camera module.

In an embodiment, as depicted in FIGS. 5-6, opposing spring fingers 16 and 18 may be electrically conductive themselves or may include electrically conductive graspers, for example a pair of diametrically opposed partial cylinder graspers 24 and 26, for grasping and connecting to the implantable medical device so that the implantable medical device can be positioned and powered simultaneously. Cylinder graspers 24 and 26 are rotatably engaged to spring fingers 16 and 18. In a first insertion position, the longitudinal axis of cylinder graspers 24 and 26 is aligned with the longitudinal axis of elongate shaft 14. In a second placement position, the longitudinal axis of cylinder graspers 24 and 26 is angled in relation to the longitudinal axis of elongate shaft 14. Each partial cylinder grasper 24 and 26 includes a raised internal ridge 36, 38, similar to that seen in FIG. 4, that engages a matching groove in the camera module 20. This ensures that the partial cylinder graspers securely grasp the camera module by providing a mechanical "lock" instead of relying solely on the friction between the interior surfaces of the partial cylinder graspers and the surface of the camera module. Other finger designs may be used to accommodate different MIS platform designs.

Figure 4:
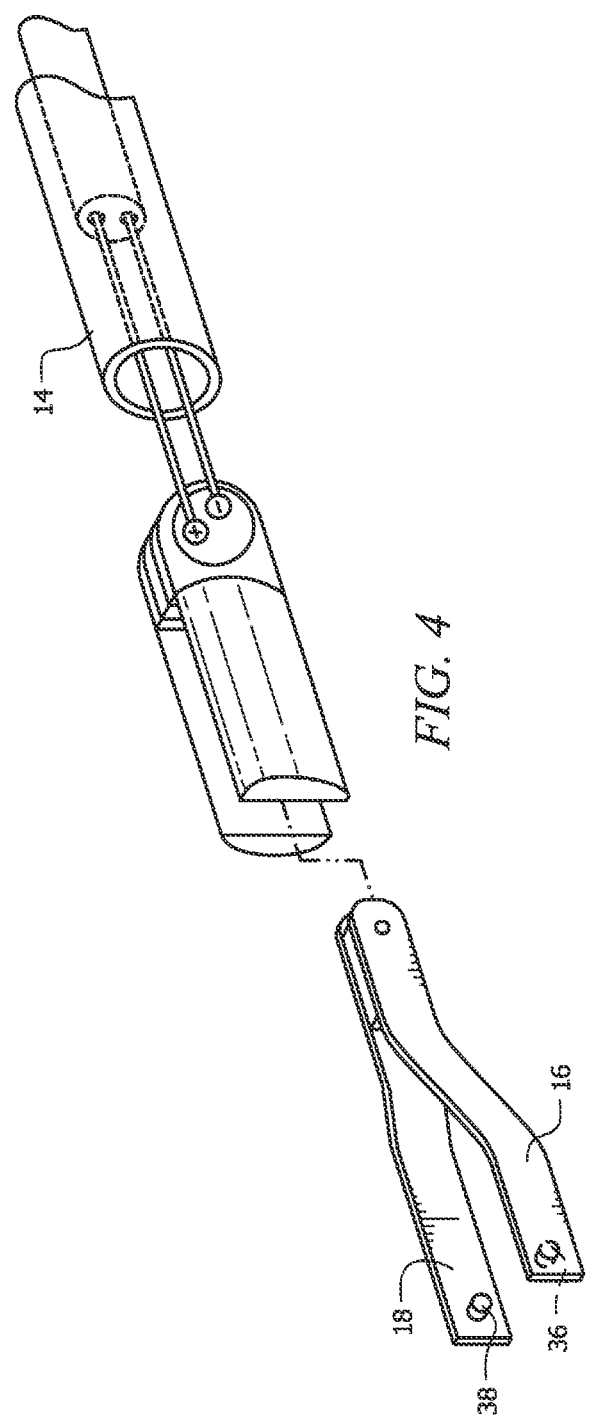
FIG. 4 is perspective view of a grasping portion of an attachment apparatus having electrical connections.

FIG. 4 further shows "+" and "−" indications, further illustrating the powering capabilities of opposing spring fingers 16 and 18 and/or graspers 26 and 26.

Figure 7:
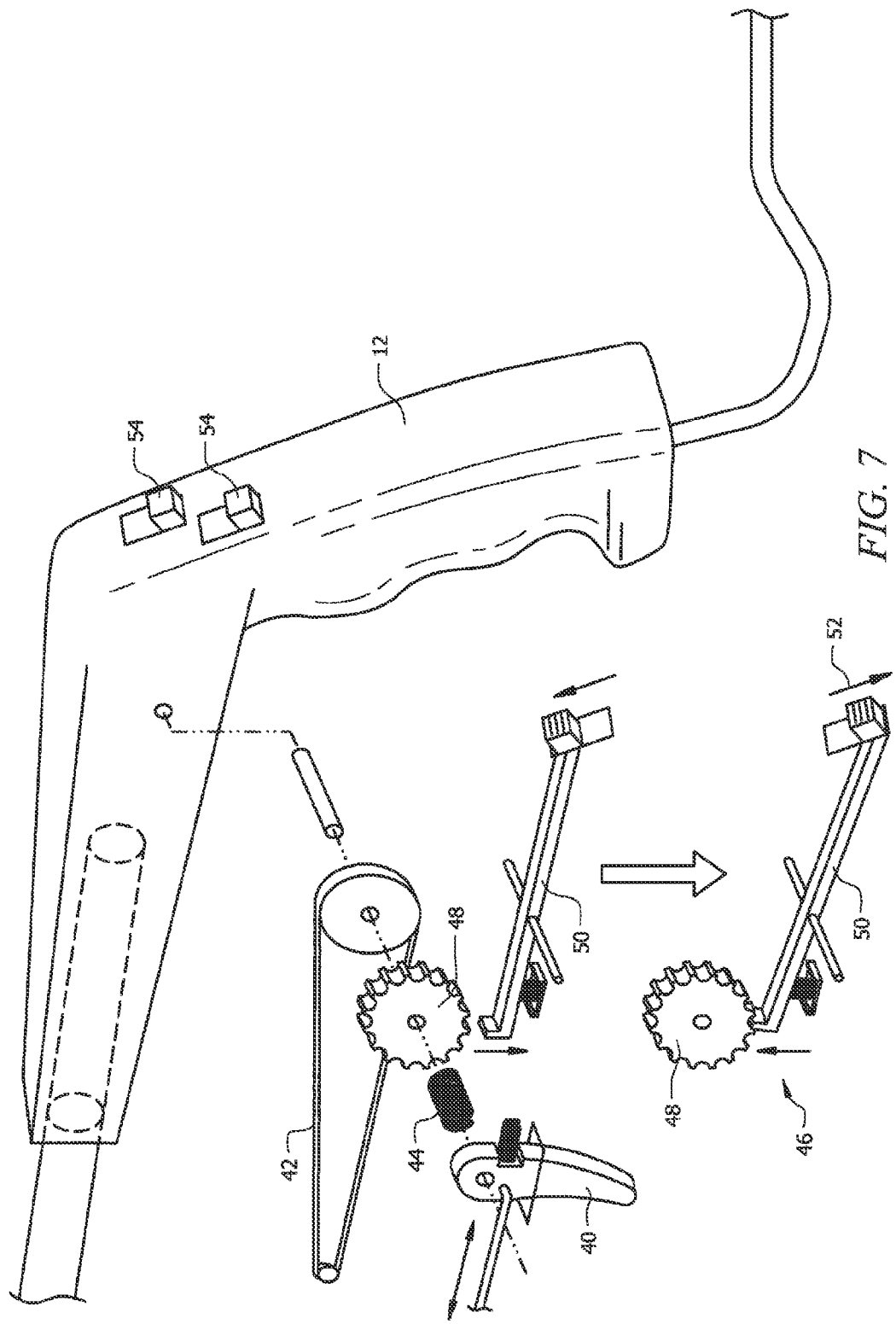
FIG. 7 is an exploded view of internal mechanisms of an attachment apparatus.
Figure 8:
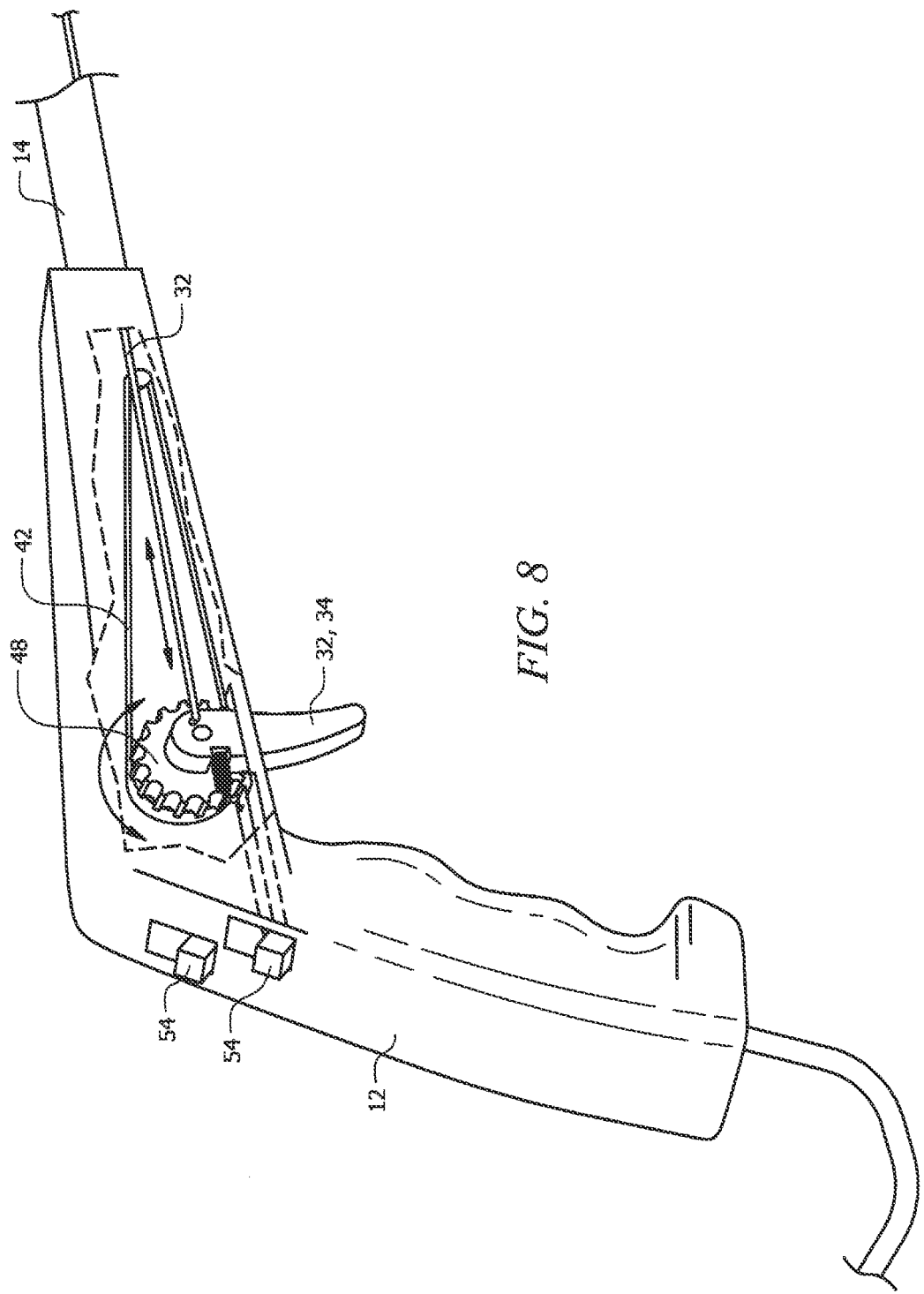
FIG. 8 is a schematic view of internal mechanisms of an attachment apparatus with one trigger mechanism shown.
Figure 9:
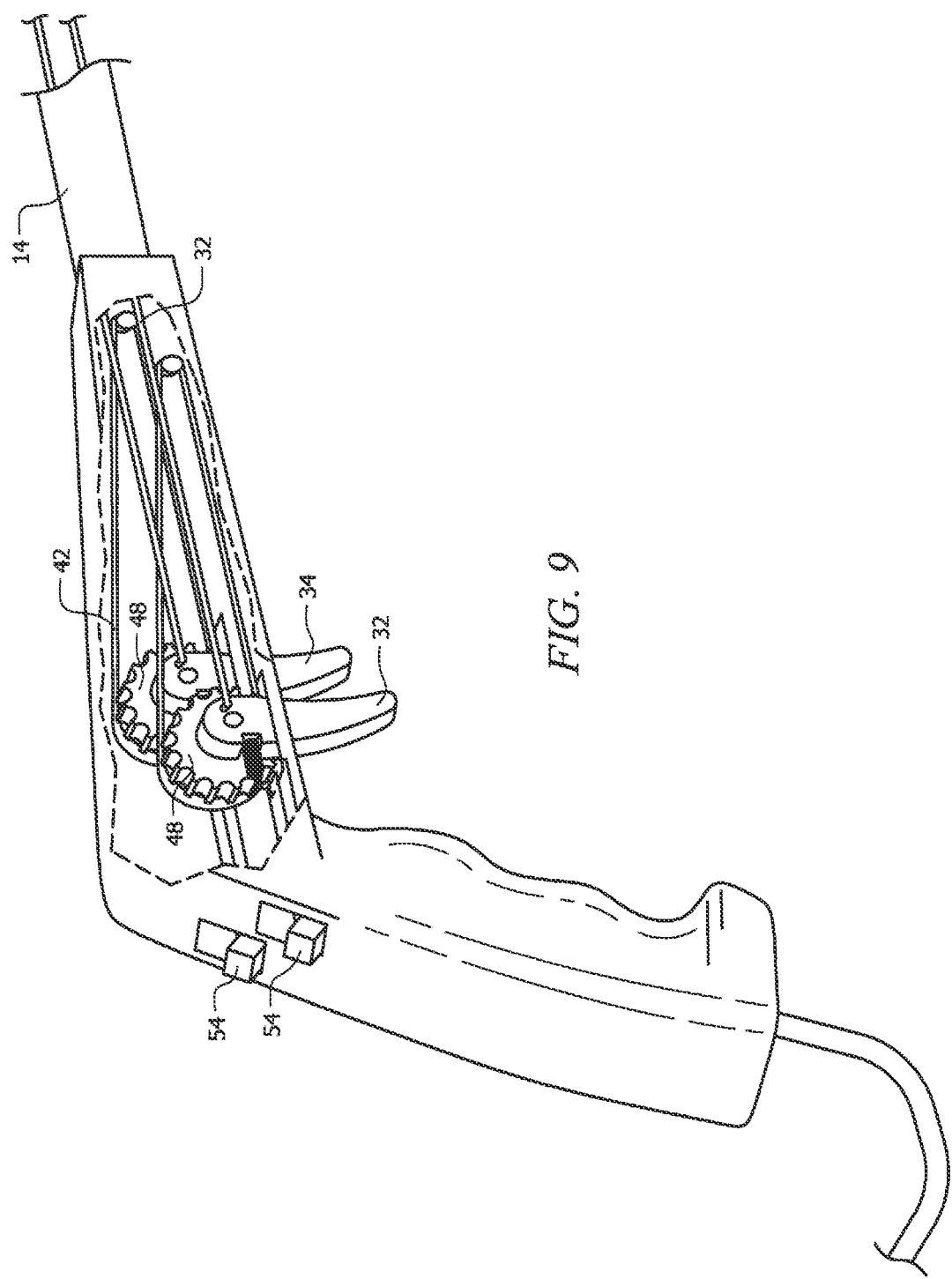
FIG. 9 is a schematic view of internal mechanisms of an attachment apparatus with two trigger mechanisms shown.

As collectively depicted in FIGS. 1-11, first trigger mechanism 32 is cooperatively positioned within handle 14 and is in mechanical communication with opposing spring fingers 16 and 18 via piston 28. Piston 28 advances and retracts opposing spring fingers 16 and 18 when first trigger mechanism 32 is engaged. As seen in FIGS. 7-9, first trigger mechanism 32 may include trigger 40, trigger actuator rod 42, and trigger spring 44. When trigger 40 is pressed, trigger actuator rod 42 engages piston 28. Piston 28 then opens and closes opposing spring fingers 16 and 18. Trigger spring 44 returns trigger 40 to its initial position after it is no longer engaged.

In an alternate embodiment, also depicted in FIGS. 7-9, cog gear and lock assembly 46 is used in conjunction with trigger 40 to incrementally engage piston 28. Spring 44 attached to cog gear 48 returns cog gear 48 to its repose position when lock 50 is released, as in the direction denoted by numeral 52. Similarly, spring 44 is attached to lock 50 and returns lock 50 to its repose position after being engaged.

In an embodiment, piston 28 includes a compression spring 30, actuating rod 32, and hard stop 34 along the inner diameter of the distal end of elongate shaft 14.

Second trigger mechanism 34 is also cooperatively positioned within the handle and is in mechanical communication with the opposing spring fingers. Second trigger mechanism 34 rotates the attached surgical device from a first insertion position to second placement position 34 when second trigger mechanism 34 is engaged. The second placement position is variable.

Second trigger mechanism 34 includes cog gear 48, lock 50, and actuator wire 42 used in conjunction with trigger 40 to incrementally rotate the attached surgical device. Spring 44 attached to cog gear 48 returns cog gear 48 to its repose position when lock 50 is released. Similarly, spring 44 is attached to lock 50 and returns lock 50 to its repose position after being engaged. Second trigger mechanism 34 is described similar to first trigger mechanism 32 and functions similarly as such, as depicted in FIGS. 7-9.

In an embodiment, linear motion can be effected to the rods or wires within the shaft to grip and release the implantable medical device, and to rotate the implantable medical device into a position to be attached to the abdominal wall or elsewhere in the surgical space. More particularly, this linear motion is created by linear movement of a trigger, which by interaction with a cog gear, results in rotational motion of the cog gear. The rod or wire is attached to the cog gear. Rotation of the cog gear results in linear motion of the rod or wire, which linear motion then grips and releases the implantable medical device, and rotates the implantable medical device into a position to be attached to the abdominal wall or elsewhere in the surgical space.

The linear motion would easily be created by a sliding mechanism, whereby the end user (e.g., surgeon, surgical assistant) would slide a "tab" on the handle of the system in a direction parallel to the axis of the shaft. The sliding mechanism would be attached to the rod or wire, directly creating linear motion of the rod or wire. The same motion could be accomplished using electromechanical linear actuators. Examples include, but are not limited to, miniature motors where the rotary motion of the motor axle is threaded, and the linear motion is created by movement of a threaded nut engaged with the threaded motor axle. A similar linear actuator could be designed based on pneumatic or hydraulic principles.

FIGS. 5 and 6 depict the distal end of the elongate shaft with the opposing spring fingers grasping camera module 20. Partial cylinder graspers 24, 26 rotate around the pivot point at the end of spring fingers 16, 18. In an embodiment, second trigger mechanism 34 rotates cog gear 48 to which is connected rod or wire 42. The rotational motion of cog gear 48 results in linear motion of rod or wire 42. The linear motion of rod or wire 42 results in rotational motion of partial cylinder graspers 24, 26 in a plane orthogonal to the axis of elongate shaft 14.

Piston 28 is withdrawn a small amount into the elongate shaft by grasping trigger 32 that is connected to the piston actuator rod 42. The other end of actuator rod 42 is connected to grasping cog gear 48. Grasping trigger 32 includes cog gear 48 and release button 54 identical to rotation trigger 34. In operation, the surgeon places camera module 20 into partial cylinder graspers 24, 26 and then engages grasping trigger 32 pulling piston 28 and flexible fingers 16, 18 into tube 14. As opposing spring fingers 16, 18 and partial cylinder graspers 24, 26 are pulled into tube 14 by piston 28 that is pulled by piston actuator rod 42, they firmly grasp camera module 20 and supply power to camera module 20. Cog gear 48 and release button 54 lock piston 28 in place, securely holding camera module 20 within spring fingers 16, 18 and partial cylinder graspers 24, 26.

Piston 28 includes compression spring 30 at its base inside elongate shaft 14. When trigger 40 is pulled, spring 30 is compressed. Cog gear 48 and release button 54 keep piston 28 in the selected grasped position. The tension on piston actuator rod 42 can be increased by pulling trigger 40 harder and further compressing compression spring 30. When release button 54 is pushed, compression spring 30 returns to repose and pushes piston 28 to its forward position, opening flexible fingers 16, 18 and releasing camera module 20.

A hard stop is located on the inner wall of the elongate shaft. The hard stop impedes piston 28 in the fully forward position while retaining some compression in compression spring 30. The position of the hard stop is indicated in the drawings but it is not shown. The hard stop is a small peripheral ridge around the inner diameter of elongate shaft 14.

FIG. 2 depicts the distal end of the elongate shaft with opposing spring fingers 16, 18 open and ready to grasp camera module 20 or other platform. Only a very small movement of piston 28 is needed to grasp and release camera module 20.

Figure 10:
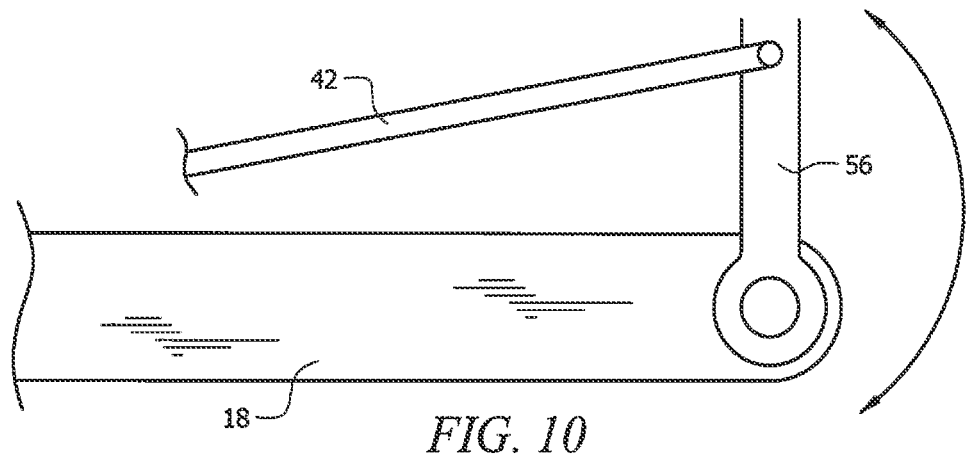
FIG. 10 is a close-up view of a spring finger of an attachment apparatus with pivot arm coupled thereto.
Figure 11:
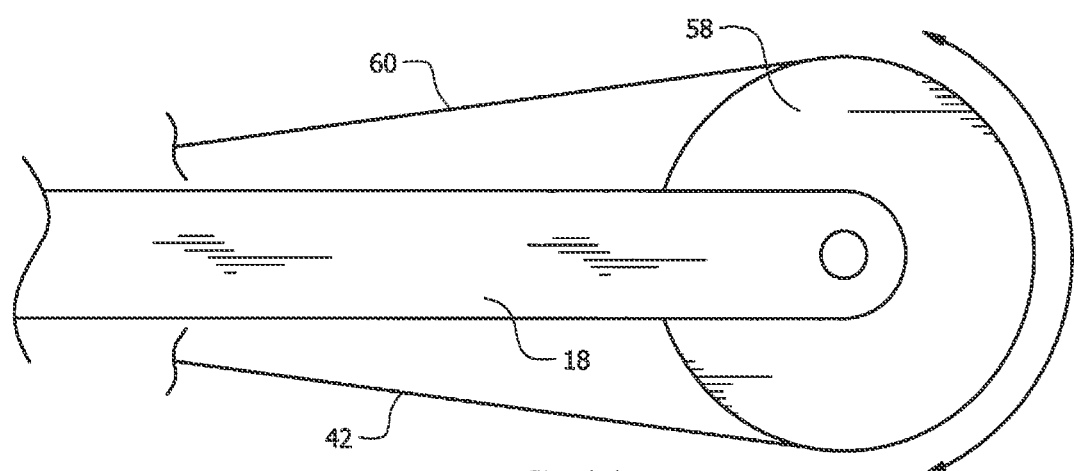
FIG. 11 is a close-up view of a spring finger of an attachment apparatus with pulley coupled thereto.

In an embodiment, the attachment apparatus includes a lever arm attached to the side of one or both partial cylinder graspers 24, 26 (alternatively, pivot arm 56 may be used, as seen in FIG. 10). Attached to the lever arm is flexible wire/rod 42. The other end of wire/rod 42 is attached to rotation cog gear 48 that is attached to second trigger mechanism 34. Camera module 20 is capable of rotating 180 degrees from the insertion position (i.e., where the longitudinal axis of camera module 20 is aligned with the longitudinal axis of elongate shaft 14). Moreover, during insertion, a camera lens on camera module 20 is positioned forward, allowing a surgeon to see where camera module 20 is being placed inside the body. After insertion, camera module 20 may be rotated via second trigger mechanism 34.

The lever arm may be replaced with pulley 58, as seen in FIG. 1, added to rotation cog gear 48. In this embodiment, the flexible wire/rod is replaced by flexible cable 60 which runs around pulley 58 attached to rotational cog gear 48. As cog gear 48 rotates, flexible cable 60 is pulled and camera module 20 rotates.

In operation, camera module 20 is inserted into opposing spring fingers 16, 18. Opposing spring fingers 16, 18 may have different configurations depending on the specific design of camera module 20. When camera module 20 is grasped by fingers 16, 18/cylinders 24, 26, contacts on the inside of the fingers/cylinders mate with contacts on the exterior of camera module 20, supplying DC voltage powering the camera module. DC voltage/power is supplied to the apparatus via a two conductor cable that exits the bottom of pistol grip handle 12.

When camera module 20 is grasped, powered, and fully operational, it is inserted into the body via a trocar port or a small incision.

It is contemplated herein that either AC or DC power can be supplied to the implantable medical device. It is further contemplated that the controllable power supplies can be either within the system itself or in a separate unit connected to the system via a cable. A connection to a separate unit may include multiple conductors in the cable.

Powering the insertable/implantable medical device by direct conduction of electricity via physical conductors comprised of fingers 16, 18 and/or grasping mechanisms 24, 26 provides several benefits. The powering mechanism allows the system to provide an unlimited variety of voltages and waveforms (DC and AC) to optimally match the power requirements of any insertable/implantable device, via a power supply integral to the system with power selectable by various means (buttons, sliders, etc.) on the system, or on a separate power supply, which would then supply the selected power voltage and waveform to the system via an electrical cord.

In an embodiment, the current invention includes two (2) separate sets of electrically-conductive elements (e.g., fingers 16, 18 and/or grasping mechanisms 24, 26) that are integral to the system or engagement/attachment tool and that establish and maintain a direct metallic electric connection between the system's conductive elements and the implantable medical device. This obviates the need for the transcutaneous passage of any electromagnetic waves. Structurally, the system's conductive elements are uniquely separated from each other to provide separate positive and negative electrically conductive paths, which conduct DC current to provide direct delivery of DC electrical current through the metallic electrically conductive components to the implantable medical device. The system directly powers the implantable device, obviating the requirement to include AC to DC conversion/rectification circuitry in the implantable device, in turn significantly increasing reliability while decreasing the size and cost of the system and implantable medical device. In an embodiment, this power can be delivered to the implantable medical device only during insertion and withdrawal of the medical device, as direct electrical connection is needed for delivering the power.

Further, the powering mechanism eliminates the potential for electromagnetic interference with other medical devices (in the area, about to be inserted/implanted, or already inserted/implanted, for example including, but not limited to, pacemakers and defibrillators), instruments, and systems that can result from an electromagnetic field created by inductively-coupled powering approaches.

An RF field electromagnetically-coupled transformer can only be implemented with alternating current (AC). Such a design requires components and circuitry to convert AC to DC, which are not required in the camera module or current system because DC power can be supplied directly to the camera module or other implantable device.

If the insertable/implantable medical device is a camera or other imaging sensor, powering the insertable/implantable device as described allows the system—with the insertable/implantable medical device attached—to function as a traditional laparoscope during insertion, implantation or attachment, de-attachment and withdrawal. This provides the surgeon with a familiar process during surgery.

In an embodiment, once the implantable medical device is inserted into the subject and attached along the abdominal wall or other targeted area, power can be supplied via a coaxial cable (see U.S. Pat. No. 8,416,342) in parallel with the power being supplied by the current system. Once the inserted medical device is receiving power via its coaxial needle, the attachment apparatus/system discussed herein can release the device and be removed through the trocar port, as the device will remain powered via its coaxial needle.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An attachment apparatus for grasping a releasably implantable medical device within a body of a patient, comprising:
    a handle and an elongate shaft mounted to said handle;
    a piston disposed within said elongate shaft;
    one or more fingers secured to a distal end of said piston, said one or more fingers adapted to grasp said releasably implantable medical device, said one or more fingers including a pair of fingers that mirror each other;
    a first mechanism in communication with said one or more fingers for retracting and advancing said one or more fingers into and out of said elongate shaft by retracting and advancing said piston where said piston and said pair of fingers conjointly move proximally and distally, such that said one or more fingers have a first position of repose within said elongate shaft and a second position of extension distal to said elongate shaft; and
    a grasper of a plurality of graspers disposed on a distal end of each finger of said pair of fingers, wherein said graspers extend laterally and toward each other from said pair of fingers, each of said graspers rotatable along a longitudinal axis of said each finger from a first insertion position to a second placement position, said second placement position being angled relative to the longitudinal axis of said elongate shaft, said each grasper adapted to be mated to a contact on said releasably implantable medical device in order to grasp said releasably implantable medical device between said graspers so that said releasably implantable medical device is angled relative to the longitudinal axis of said elongate shaft when said grasper is disposed in said second placement position,
    said first mechanism enabling the grasping or release of said implantable medical device by said graspers when said first mechanism is engaged,
    whereby a surgeon can insert and place said releasably implantable medical device in said patient by engaging said first mechanism in communication with said one or more fingers, such that said implantable medical device is powered through said apparatus during insertion of said implantable medical device, is fully functional, and can be released into said patient.

2. An apparatus as in claim 1, further comprising:
    said each grasper having a partial cylinder shape.

3. An apparatus as in claim 2, further comprising:
    said each grasper having a locking ridge on an inner surface of said each grasper.

4. An apparatus as in claim 1, further comprising:
    a power source in direct electrical connection with said each grasper, said graspers supplying electricity to said releasably implantable medical device when grasped by said graspers.

5. An apparatus as in claim 1, further comprising:
    a hard stop disposed within said elongate shaft.

6. An apparatus as in claim 1, further comprising:
    said first mechanism being a trigger mechanism that includes a spring loaded cog gear and lock.

7. An apparatus as in claim 1, further comprising:
    a second mechanism cooperatively positioned relative to said handle and in mechanical communication with said one or more fingers, said second mechanism rotating said one or more fingers from said first insertion position to said second placement position when said second mechanism is engaged.

8. An apparatus as in claim 1, further comprising:
    said first mechanism including a reciprocating means in communication with said one or more fingers for retracting and advancing said one or more fingers into and out of said elongate shaft.

9. An apparatus as in claim 1, further comprising:
    a means of rotating said each grasper on said each finger.

10. An attachment apparatus for grasping and powering a releasably implantable medical device within a body of a patient, comprising: a handle and an elongate shaft mounted to said handle;
    a piston disposed within said elongate shaft;
    one or more fingers secured to a distal end of said piston, said one or more fingers including a pair of fingers that mirror each other, piston and said pair of fingers conjointly moving proximally and distally during contraction and expansion of said pair of fingers;
    a grasper of a plurality of graspers attached to a distal end of each of said pair of fingers, wherein said graspers extend laterally and toward each other from said pair of fingers, each of said graspers rotatable along a longitudinal axis of said each finger said graspers adapted to be mated to contacts on said releasably implantable medical device in order to grasp said releasably implantable medical device between said graspers;
    a power source in direct electrical connection with said each grasper, said grasper adapted to supply power to said releasably implantable medical device when grasped by said graspers,
    whereby said apparatus assists a surgeon in insertion and placement of said releasably implantable medical device such that said medical device is powered through said apparatus, is fully functional, and can be released into a patient.

11. An apparatus as in claim 10, further comprising:
    a rotating mechanism in communication with said one or more fingers, said rotating mechanism enabling the grasping or release of said implantable medical device when said rotating mechanism is engaged; and
    a means of rotating said graspers along the longitudinal axis of each finger, said means of rotating said graspers rotating said graspers from a first insertion position to a second placement position when said second mechanism is engaged, said second placement position being angled relative to the longitudinal axis of said elongate shaft.

12. An attachment apparatus for grasping and powering a camera module within a body of a patient, comprising:
  a handle and an elongate shaft mounted to said handle;
  a piston disposed within said elongate shaft;
  a pair of opposing spring fingers that mirror each other and open and close relative to one another, said pair of opposing spring fingers secured to a distal end of said piston, said pair of opposing spring fingers and said piston being partially and slideably disposed within a distal end of said elongate shaft opposite said handle;
  a pair of diametrically opposed partial cylinder graspers, each grasper of said pair of graspers disposed on a distal end of each finger of said pair of fingers, said pair of graspers extending inwardly, laterally, and toward each other from said each finger, said graspers adapted to be mated to contacts on said camera module in order to grasp said camera module;
  a first trigger mechanism cooperatively positioned relative to said handle and in mechanical communication with said pair of opposing spring fingers via said piston, said piston advancing and retracting said pair of opposing spring fingers into and out of said elongate shaft when said first trigger mechanism is engaged where said piston and said pair of fingers conjointly move proximally and distally, such that said pair of opposing spring fingers have a first position of repose within said elongate shaft and a second position of extension distal to said elongate shaft;
  a second trigger mechanism cooperatively positioned relative to said handle and in mechanical communication with said pair of opposing spring fingers, said second trigger mechanism rotating said pair of opposing spring fingers from a first insertion position to a second placement position when said second trigger mechanism is engaged;
  a means of rotating said graspers along a longitudinal axis of each finger, said means of rotating said graspers rotating said graspers from said first insertion position to said second placement position, said a second placement position being angled relative to a longitudinal axis of said elongate shaft so that said camera module is angled relative to the longitudinal axis of said elongate shaft when said grasper is disposed in said second placement position, said first mechanism enabling the grasping or release of said camera module by said grasper when said first mechanism is engaged;
  a power source in direct electrical connection with said each grasper, said power source transmitting electricity to said camera module through said each grasper when grasped by said each grasper,
  whereby a surgeon can insert and place said camera module in said patient by engaging said first trigger mechanism and said second trigger mechanism in communication with pair of opposing spring fingers, such that said camera module is powered through said attachment apparatus, is fully functional, and can be released into said patient.

\* \* \* \* \*